United States Patent [19]

Lankow et al.

[11] Patent Number: 5,047,207
[45] Date of Patent: Sep. 10, 1991

[54] KIT FOR DIAGNOSING PLANT DISEASES

[75] Inventors: Richard K. Lankow, Cinnaminson; Sally A. Miller, Pennsauken; G. David Grothaus, Delran; Frank P. Petersen, Beverly, all of N.J.; Dennis R. Stocker, Yardley, Pa.; Stephanie L. Papa, Merchantville, N.J.; James Donovan, Levittown; Douglas Malik, Pittsburgh, both of Pa.

[73] Assignee: Agri-Diagnostics Associates, Cinnaminson, N.J.

[21] Appl. No.: 865,379

[22] Filed: May 20, 1986

[51] Int. Cl.$^5$ .............................................. G01N 1/02
[52] U.S. Cl. .......................................... 422/58; 422/56; 422/61; 435/7.1; 436/503; 436/527; 51/402; 51/395; 51/406; 73/864.41
[58] Field of Search ................... 422/56, 58, 61; 436/501, 503, 527, 538, 548, 808, 810, 824; 51/275, 301; 206/438; 604/398, 390; 435/291

[56] References Cited

U.S. PATENT DOCUMENTS

| Re. 29,725 | 8/1978 | Johnson et al. | 23/230 |
|---|---|---|---|
| 847,190 | 3/1907 | Landis | 51/395 |
| 875,936 | 1/1908 | Landis | 51/395 |
| 2,985,288 | 5/1961 | Reich | 206/46 |
| 3,469,958 | 9/1969 | Johnson | 51/301 X |
| 3,890,204 | 6/1975 | Avery | 195/139 |
| 3,955,926 | 5/1976 | Fischer | 23/230 |
| 3,965,888 | 6/1976 | Bender | 422/58 X |
| 4,076,502 | 2/1978 | Dugle et al. | 422/58 X |
| 4,244,940 | 1/1981 | Jeong et al. | 422/61 X |
| 4,259,964 | 4/1981 | Levine | 128/638 |
| 4,273,741 | 6/1981 | Levine | 422/56 |
| 4,303,610 | 12/1981 | Sardisco et al. | 422/61 |
| 4,305,924 | 12/1981 | Piasio et al. | 424/1 |
| 4,420,353 | 12/1983 | Levine | 156/227 |
| 4,429,050 | 1/1984 | Yasuda et al. | 436/805 X |
| 4,471,058 | 9/1984 | Smith et al. | 436/808 X |
| 4,605,404 | 8/1986 | Sneider | 604/389 X |

FOREIGN PATENT DOCUMENTS 0113075 7/1984 European Pat. Off. .

Primary Examiner—Sam Rosen
Attorney, Agent, or Firm—Pennie & Edmonds

[57] ABSTRACT

A method and a kit for testing a plant for a suspected antigen. A sample of the plant is taken and rubbed between first and second pads to extract sap from the sample and to collect the sap on the first pad. The sap is transferred to a liquid solution, and that solution is tested for the suspected antigen. This may be done by contacting the solution with a tag antibody and with a carrier having a capture antibody so that a tag antibody-antigen-capture antibody complex forms on the carrier if the suspected antigen is in the liquid solution. The carrier is then tested for the tag antibody. The kit preferably includes the first and second pads, the carrier, containers to hold the liquid solution and the tag antibody, and a device or reagent to test the carrier for the tag antibody.

5 Claims, 2 Drawing Sheets

1

KIT FOR DIAGNOSING PLANT DISEASES

BACKGROUND OF THE INVENTION

This invention generally relates to the diagnosis of plant diseases; and, more specifically, to a method especially well suited for the field diagnosis of plant diseases, and to a kit including the materials needed to carry out that method.

Plant diseases cause a tremendous amount of damage and economic loss each year. For example, it certain types of grass diseases, such as pythium blight, become wide spread over a particular area, it may be necessary to remove and to replace all the grass in the affected area. Even if this is not necessary, an extensive amount of time and treatment may be required to control the disease.

The magnitude of the problem is caused, in part, by the fact that heretofore it has been very difficult or prohibitively expensive to diagnose most plant diseases until the symptoms of the diseases became visible. In particular, very few plant diseases can be diagnosed in a laboratory before the symptoms of the diseases become visible in the field, and most such laboratory tests are expensive and time consuming. Consequently, these tests are not normally performed until there is visible evidence in the field that a plant may be infected; and as a result, in most instances, by the time a disease is finally diagnosed, it is quite widespread.

Numerous comparatively simple and inexpensive diagnostic tests have been successfully developed using antibodies to detect human and animal diseases in very early stages of infection. To do this, a first antibody, which is reactive with a selected antigen that is, or is associated with, a disease causing organism, may be immobilized on a solid support member; and then a sample liquid solution, which is suspected of harboring the selected antigen, is contacted with the immobilized antibody. If the selected antigen is present in the sample liquid solution, the antigen reacts with and becomes bound to the first antibody to form an antigen-antibody binary complex on the solid support member.

After washing the unreacted material from the support member, the binary complex is contacted with a second, labeled antibody that is also reactive with the selected antigen. If the binary complex is present on the solid support, this second antibody reacts with and becomes bound to the antigen component of the complex to form an antibody-antigen-antibody tertiary complex. After washing the solid support member to remove any of the second antibody that did not react with the selected antigen, the support member is tested for the second antibody by any of a variety of analytical techniques.

Diagnostic procedures of the above-outlined type have been successfully developed using polyclonal and monoclonal antibodies to detect antigens associated with particular diseases with a very high degree of reliability. Monoclonal antibodies are made via a process, referred to as hybridoma technology, in which hybridomas are formed by the fusion of short-lived antibody producing cells (usually spleen cells) and long-lived myeloma cells to produce long-lived antibody synthesizing cell lines. Each hybrid cell line produces a unique and characteristic antibody that has the ability to bind, with a very high degree of specificity, to a single type of antigen.

The cells that are fused to form a particular hybridoma cell line can be selected or treated so that the monoclonal antibody synthesized by that cell line will bind only to a chosen antigen. If such an antibody is used in the above-discussed procedure as either the first or second antibody, then the antibody-antigen-antibody tertiary complex will form on the solid support member, with a very high degree of accuracy, if and only if the chosen antigen is present in the sample liquid solution Polyclonal antibodies with the appropriate affinity and specificity may also be used to detect antigens with a very high degree of accuracy.

Procedures of the above-outlined general type have been successfully employed on a commercial basis in the laboratory to test for human and animal diseases, among other things. Because of the relative simplicity and accuracy of procedures of this type, it would be very desirable to provide similar tests to diagnose plant diseases. Unique problems have been encountered, though, in developing commercially practical procedures, of the above-discussed general type, for the field diagnosis of plant diseases. For instance, it has been difficult to develop a simple and inexpensive yet field-effective technique for preparing a suitable liquid solution containing an effective quantity of a plant material that may be tested to indicate reliably whether the plant is infected with a particular antigen.

SUMMARY OF THE INVENTION

An object of this invention is to provide a very simple, inexpensive and reliable procedure to test plants for diseases.

Another object of the present invention is to provide a plant disease diagnostic procedure that is very well suited for use in the field.

A further object of this invention is to rub a plant sample between a pair of extraction pads to quantitatively collect sap from the plant on one of those pads, to transfer the sap to a liquid solution, and then to test that liquid solution for the presence of a suspected antigen to determine whether the plant is harboring that antigen.

These and other objectives are attained with a method for testing a plant for the presence of a suspected antigen, comprising the steps of taking a sample of a plant, rubbing the sample between first and second extraction pads to extract sap from the sample, and collecting the sap on the first extraction pad. The sap is transferred to a liquid solution from the first extraction pad, and then that liquid solution is tested for the presence of the suspected antigen.

With one embodiment, this testing is done by contacting the liquid solution with a tag antibody reactive with the suspected antigen and with a carrier body having attached thereto a capture antibody also reactive with the suspected antigen. A tag antibody-antigen-capture antibody complex forms on the carrier body if the suspected antigen is present in the liquid solution, and then the carrier body is tested for the presence of the tag antibody. The tag and capture antibodies may both be monoclonal antibodies, they may both be polyclonal antibodies, or one may be a monoclonal antibody while the other one is a polyclonal antibody.

A kit for carrying out the method of this invention comprises the first and second extraction pads, and a container holding the above-mentioned liquid solution and which is adapted to receive the first extraction pad to transfer sap therefrom to the liquid solution. The kit may further include the carrier body, a supply of tag antibody, and means to test the carrier body for the presence of the tag antibody. Preferably, all the parts of the kit are neatly and securely packed in a small, easily carried box.

Further benefits and advantages of the invention will become apparent from a consideration of the following detailed description given with reference to the accompanying drawings, which specify and show preferred embodiments of the invention.

DETAILED DESCRIPTION OF THE PREFERRED EMBODIMENT

Figure 1:
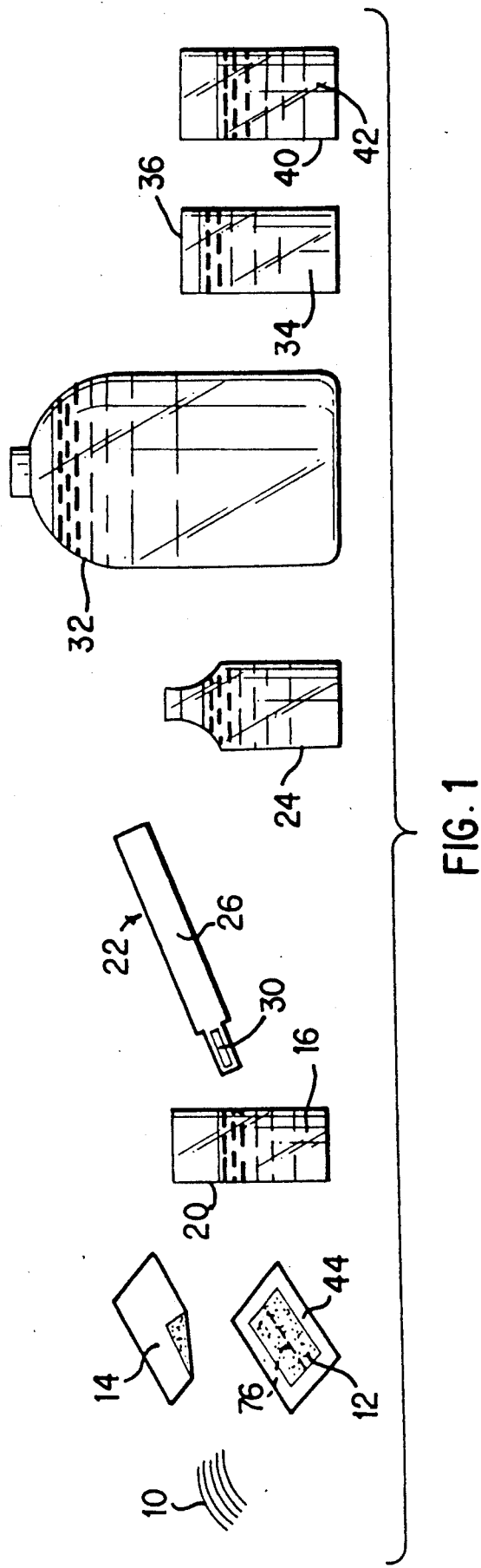
FIG. 1 is a schematic view showing equipment used to carry out the method of the present invention.

In accordance with the present invention, and with reference to FIG. 1, to test a plant for a suspected antigen, a sample 10 of the plant is taken and rubbed between first and second extraction pads 12 and 14 to extract sap from the sample. The sap is collected on first extraction pad 12 and transferred therefrom to liquid solution 16, which preferably is held within a container or tube 20, and then that liquid solution is tested in any suitable way for the presence of the suspected antigen.

With one embodiment of the invention, solution 16 is tested for the suspected antigen by contacting the liquid solution with a first, labelled antibody reactive with the suspected antigen, and with carrier body 22 having attached thereto a second antibody also reactive with the suspected antigen. The first antibody, which is preferably taken from a solution in bottle 24, is referred to as a tag antibody, and the second antibody is referred to as a capture antibody. If the suspected antigen is present in liquid solution 16, the antigen reacts with and becomes attached to both the tag antibody and the capture antibody to form a tag antibody-antigen-capture antibody complex on or attached to carrier body 22. Carrier body 22 is then tested for the presence of the tag antibody, and any of a variety of analytical techniques may be employed to do this.

Preferably, carrier body 22 used in the practice of this invention includes a thin, elongated stick 26, referred to as a dipstick, and a first end of this stick is provided with a membrane 30 that contains the capture antibody. Liquid solution 16 is contacted with this carrier body 22 by simply lowering this first end of the stick into container 20 to immerse membrane 30 into the liquid solution. To insure adequate exposure of the capture antibody to liquid solution 16, preferably membrane 30 is left to soak in the liquid solution for an extended period such as about two hours.

When carrier body 22 is immersed in liquid solution 16, some tag antibody will normally become attached to the carrier body by means other than a reaction with and attachment to the suspected antigen. Thus, when carrier body 22 is removed from liquid solution 16, normally tag antibody will be on the carrier body even if the suspected antigen is not in the liquid solution and has not become attached to the carrier body. The presence of such unreacted tag antibody on carrier body 22, in the absence of the suspected antigen, is undesirable since it may lead to a false conclusion about the presence of the suspected antigen on the carrier body. Specifically, with the preferred embodiment of the invention described herein, carrier body 22 is directly tested for the tag antibody, with the presence of that antibody indicating indirectly that the suspected antigen is also on the carrier body. Hence, if tag antibody, but not the suspected antigen, is on carrier body 22, a person may mistakenly conclude that the suspected antigen is on the carrier body.

For this reason, preferably carrier body 22 is carefully washed or rinsed after being removed from solution 16 to remove from the carrier body all the unreacted tag antibody—that is, all the tag antibody that is attached to the carrier body by means other than a reaction with the suspected antigen. In this way, all the tag antibody, if any, that remains on carrier body 22 is attached to it via the suspected antigen, and a subsequent test that shows that the tag antibody is on the carrier body reliably indicates that the suspected antigen is also on that carrier body. With a recommended technique, after carrier body 22 is removed from solution 16, the carrier body, specifically membrane 30, is carefully sprayed with a rinse solution from bottle 32, then soaked in solution 34 in container or tube 36 for a period of about five minutes, and then again thoroughly sprayed with the rinse solution from bottle 32.

Any suitable procedure may be used to test carrier body 22 for the presence of the tag antibody. For example, the tag antibody may include an enzyme conjugate that reacts with a selected enzyme substrate to produce a product having a particular color, and membrane 30 may be soaked in a container or tube 40 having a solution 42 containing the selected enzyme substrate to see if this color is produced on the membrane 30 as a result of the catalytic activity of the enzyme. If the color is produced, or produced to a certain intensity, the user can conclude that the tag antibody is on carrier body 22, and thus that the suspected antigen is on the carrier body and in plant sample 10 used in the diagnostic test. Conversely, if this particular color is not produced, or not produced to that certain intensity, when membrane 30 is immersed in the solution 42, the tag antibody is not present on carrier body 22, indicating that plant sample 10 is free of the suspected antigen. With this technique, the intensity of the color produced on membrane 30 also is an indication of the degree to which plant sample 10 is harboring the suspected antigen.

If desired, a test may be done using the above-described procedure except that no plant sample is rubbed between extraction pads 12 and 14. Such a negative control test may be desirable to determine if the test procedure is being properly performed, and to indicate the extent, if any, to which carrier body 22 will turn a particular color by means other than a reaction with the enzyme substrate and the tag antibody-suspected antigen-capture antibody complex. A positive control test, using a liquid solution 16 known to contain the suspected antigen at an appropriate concentration, can be done to be sure the antigen can be detected on carrier body 22.

Various types of extraction pads may be used in the practice of this invention. For example, first extraction pad 12 may be a flat sheet of material secured to a backing 44 that provides support for the first extraction pad as it is rubbed against the plant sample. With this arrangement, the sap collected on pad 12 is transferred therefrom to liquid solution 16 by removing the first extraction pad from backing 44 and placing this extraction pad in the liquid solution. Preferably, tube 20 is then covered and thoroughly shaken to insure an adequate transfer of any of the suspected antigens on extraction pad 12 to liquid solution 16; and, after this, tube 20 is uncovered and extraction pad 12 is simply removed from the tube and discarded.

Preferably, both first and second extraction pads 12 and 14 are flat sheets of abrasive paper. It is desirable, though, to avoid making extraction pads 12 and 14 from materials that might break apart, or that have an abrasive that might come off, either as the plant sample is rubbed between extraction pads 12 and 14, or when pad 12 is in solution 16. With an embodiment of the invention that has been actually reduced to practice, the first extraction pad is a flat sheet of emery paper, approximately ¾ inches by 2 ⅛ inches, peelably secured to a firm cardboard backing 44, and second extraction pad 14 is a flat sheet of emery paper about 1 ⅜ inches by 1 inch. In use, the plant sample 10 is simply rubbed between these first and second extraction pads 12 and 14 until the first extraction pad is thoroughly covered with sap, and then the first extraction pad is peeled from support backing 44 and placed in liquid solution 16.

Extraction pads 12 and 14 disclosed herein effectively accomplish a number of seemingly conflicting objectives. These pads 12 and 14 disrupt the physical integrity of plant sample 10 to the extent necessary to extract sap and antigen therefrom. Also, the sap and antigen are effectively collected on first extraction pad 12, eliminating the need for an additional, separate piece of equipment to hold or carry the extracted sap. At the same time, despite the abrasive nature of first extraction pad 12, antigen will pass from this pad and into solution 16, which is a form very well suited for many conventional analytical procedures. The size of first extraction pad 12 may be used to control the amount of sap added to liquid solution 16, and the size of pad 12 can be chosen to help insure an adequate amount of sap is taken so that the test results are reliable. Further, extraction pads 12 and 14 are very small, light and inexpensive.

The method of this invention is relatively simple and may be carried out by an individual without elaborate training or instructions. Also, the method is very easy to perform in the field, and does not require any expensive, heavy or cumbersome equipment. Indeed, all the equipment needed to carry out the method may be provided in a small, lightweight kit, described below, that is very easy to carry around from place to place.

Figure 2:
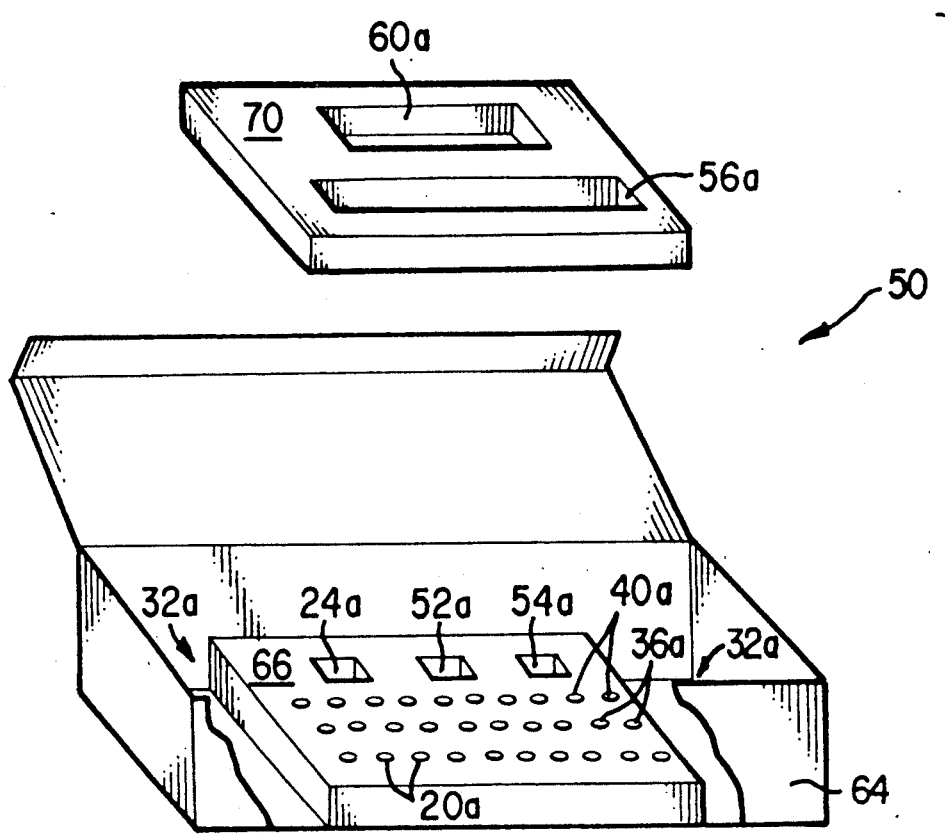
FIG. 2 is a perspective view of a kit that may be used to practice this invention.
Figure 2:
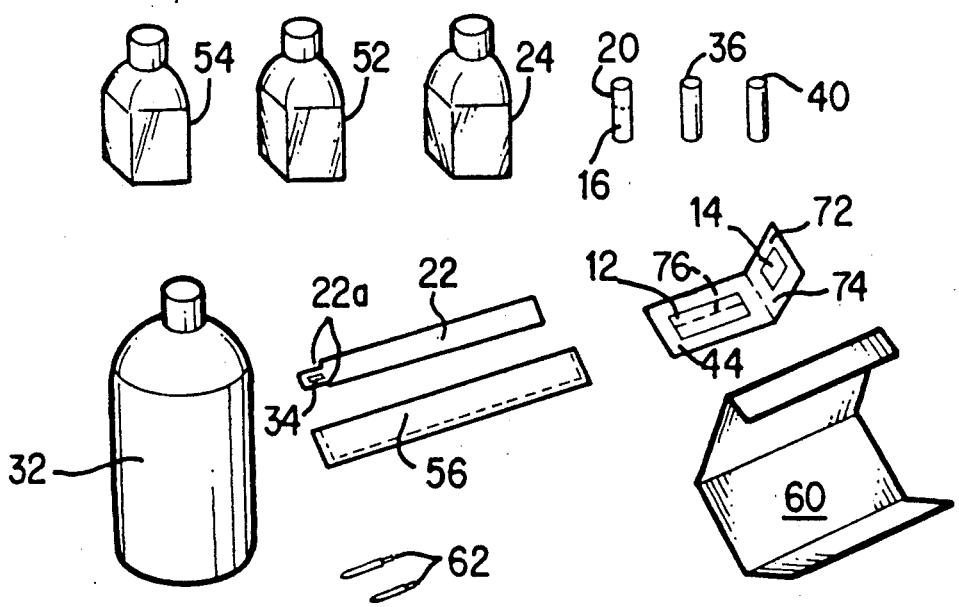

FIG. 2 illustrates kit 50 that may be employed to carry out the process of this invention; and, generally, the kit includes extraction pads 12 and 14, container 20 holding solution 16, and means to test that solution for the presence of the suspected antigen. Preferably, this testing means includes carrier body 22 and bottle 24 holding the tag antibody, and kit 50 further includes a pair of rinse bottles 32 (only one is shown in FIG. 2), rinse tube 36, and color reaction tube 40.

Extraction pads 12 and 14, solution 16, the tag antibody in bottle 24, carrier body 22, rinse bottles 32, and rinse tube 36 are used as described above so that if a suspected antigen is present in a tested plant sample, a tag antibody-antigen-capture antibody complex forms on the carrier body. The tag antibody provided in kit 50 includes a horseradish peroxidase conjugate; and, to detect that tag antibody on carrier body 22, tube 40 of kit 50 holds a peroxidase substrate, and the kit includes bottle 54 holding a source of peroxide such as a hydrogen peroxide solution.

To detect the tag antibody on carrier body 22, the solution in bottle 54 is added to the solution in tube 40, to a suitable predetermined level, and the membrane 30 on carrier body 22 is inserted into the mixed solution in tube 40. If a color is produced on membrane 30, then the tag antibody is present thereon; but if no color is produced on the membrane, then the membrane is free of the tag antibody and the suspected antigen.

A preferred embodiment of kit 50 is designed to hold supplies for ten diagnostic tests. Thus kit 50 includes ten each of pads 12 and 14, tubes 20, 36 and 40, and carrier body 22; and bottles 24, 32, and 54 hold a sufficient quantity of materials for ten tests. Only one each of pads 12 and 14, tubes 20, 36 and 40, and carrier body 22 are shown in FIG. 2, though, in order to simplify the figure. Each carrier body 22 may be enclosed within a first protective envelope 56, and each pair of extraction pads 12 and 14 may be enclosed within a second protective envelope 60. A plurality of bags (not shown) or other containers may be provided in kit 50 to collect and hold the plant samples. Bottles 24 and 54 may be flexible, squeeze bottles including top discharge openings; and solution from bottle 24 may simply be squeezed therefrom into solution 16, and solution from bottle 54 may be squeezed therefrom into tube 40.

Box 64 is provided to hold the components of kit 50; and styrofoam base 66 is provided to facilitate packing, shipping and handling the various pieces of equipment in the kit. Base 66 includes recesses 20a, 36a, 40a, 24a and 54a; and in an assembled position, base 66 is located in the bottom of box 64, with tubes 20, 36 and 40 respectively located in recesses 20a, 36a and 40a, and with bottles 24 and 54 respectively held in recesses 24 and 54a. Also, base 66 includes a recess 56a for holding envelopes 56, and recess 60a for holding envelopes 60; and box 64 form compartments 32a, at the ends of the box, for securely holding bottles 32. In addition, as will be appreciated, preferably box 64 folds to a closed position with all of the pieces of kit 50 neatly and securely held therewithin.

With the embodiment of the extraction means shown in FIG. 2, first extraction pad 12 is secured to support backing 44, and second extraction pad 14 is connected to its own support backing 72. Backing 72 is connected to backing 44 to keep first and second extraction pads 12 and 14 together until they are used, and a tear line 74 may be formed at the connection between backings 44 and 72 to help tear apart those backings to use the extraction pads.

Extraction pad 12 may be provided with a central longitudinal fold line 76 so that the pad may be folded about this line to reduce its overall size to help insert the extraction pad into tube 20. In the embodiment of the invention where first extraction pad 12 is peelably removed from backing 44, preferably, when this is done, some adhesive material remains on the back surface of pad 12 —that is, the surface thereof which is in direct contact with the support backing 26. This adhesive is helpful in that it may be used to hold the two sides of the back surface together when extraction pad 12 is folded about line 76.

Liquid solution 16 is a buffer solution such as a tris-buffered saline solution; and, advantageously, the solution 16 is one which helps to extract the suspected antigen from extraction pad 12. Solution 16 may also be provided with an anti-bonding agent, commonly referred to as a blocking agent, that inhibits the attachment of the tag antibody directly to carrier body 22. Preferably, the pH of solution 16 is between about 5 and 9, and it is believed that it is best to keep the pH of this liquid solution between about 6.5 and 7.5.

The solution in container 24 is a buffered saline solution, and preferably is supplemented with proteins to protect the antibody in the solution. Preferably, the pH of the solution in container 24 is between about 5 and 9, and even more preferably, is kept between about 6.5 and 7.5. The tag antibody may be transferred to solution 16 from container 24 in any acceptable manner. For example, a small amount of solution may be aspirated into a pipette or dropper from container 24, and then dispensed into solution 16 from the pipette or dropper. After the tag antibody is added to solution 16, tube 20 is preferably capped and well shaken to insure an adequate distribution of the tag antibody throughout solution 16. The solutions in bottle 32 and tube 36 are also buffered saline solutions, and the same solution may be used in both bottle 32 and tube 36. Preferably, the pH of these solutions is between 5 and 9, and it is believed that best results are obtained if that pH is between 6.5 and 7.5.

Various alternate types of carrier bodies may be used in the practice of this invention. For example, the carrier body may be a test tube having the capture antibody coated to the inside surface of the tube, or the carrier body may comprise plastic beads or circular disks having the capture antibody coated on the outside surfaces of the beads or disks. Also, the carrier body may be a microtitre plate having a multitude of wells coated with the capture antibody. Dipstick type carrier bodies are preferred, though, because such sticks are very easy to handle and to wash, and have proven to be very efficient and cost effective.

Preferably, membrane 30 comprises a nitrocellulose or nylon material embedded with large quantities of antibodies, and the membrane is secured to stick 26 by a conventional adhesive such as a flat piece of tape having adhesive on both faces thereof. Care should be taken, though, to avoid using an adhesive that destroys or renders inactive the suspected antigen or the tag or capture antibodies. Any suitable technique may be employed to imbed the antibodies in membrane 30. Preferably, when or after the capture antibody is imbedded in membrane 30, the membrane is treated with a blocking agent to fill antibody attachment sites on the membrane that are not filled with the capture antibody. This blocking agent helps to keep free tag antibody in solution 16 —that is, tag antibody that has not reacted with the suspected antigen— off of the membrane 30.

A conventional reflectometer (not shown) may be provided in kit 50 to measure the intensity of the color, if any, that develops on membrane 30; and if such a meter is used, the size of the membrane should be such that it can be properly used with the meter. Lateral shoulders 22a may be formed on carrier body 22 to limit the extent to which membrane 30 can be inserted into the reflectometer, and thus to help properly position the membrane in the meter.

Various combinations of monoclonal and polyclonal antibodies may be used in the practice of the present invention. For instance, the tag and capture antibodies may both be monoclonal antibodies, or they may both be polyclonal antibodies. Alternately, the tag antibody may be a monoclonal antibody while the capture antibody is a polyclonal antibody, or the capture antibody may be a monoclonal antibody while the tag antibody is a polyclonal antibody.

The antibodies utilized in the practice of this invention may be made or obtained in any suitable manner. For example, U.S. Pat. Nos. 773,811 filed Apr. 19, 1984, and 834,198 filed Aug. 8, 1985, disclose several procedures for making suitable monoclonal antibodies that may be used in this invention.

Preferably, the labeling enzyme used with the tag antibody is selected from the group comprising a peroxidate beta galactosidase, alkaline phosphatase or urease. Suitable enzyme substrates for a peroxidase include 0-phenylimine, diamine, 0-toluadine, 4-chloronaphthol or ABTS. Suitable enzyme substrates for beta galactosidase include para or ortho nitrophenol-d-galactose. Urea is a suitable substrate for urease, and paranitrophenol phosphate is a suitable substrate for alkaline phosphatase.

Numerous suitable arrangements other than the ones specifically described above, may be employed to detect the presence of the suspected antigen in solution 16. For instance, if desired, carrier body 22 may be contacted with solution 16 to develop an antigen-capture antibody complex on the carrier body, and then contacted with the tag antibody —either in solution 16 or in a separate solution— to produce the tag antibody-antigen-capture antibody complex on the carrier body. Also, if the suspected antigen is itself directly detectable on the carrier body 22, the use of the tag antibody may be eliminated.

The plant sample 10 used in the practice of this invention may be taken in any suitable way. For instance, if the plant is a grass, blades, roots or stems of the grass may be cut or pulled from the ground and used as the plant sample. Alternatively, if the plant is a tree, leaves may be pulled or cut from the tree and used as the plant sample. Regardless of the specific type of sample that is used, it should be carefully identified, and the location of the plant from which the sample is taken should be carefully recorded.

While it is apparent that the invention disclosed herein is well calculated to fulfill the objects previously stated, it will be appreciated that numerous modifications and embodiments may be devised by those skilled in the art, and it is intended that the appended claims cover all such modifications and embodiments as fall within the true spirit and scope of the present invention.

What is claimed is:

1. Apparatus for extracting and collecting sap from a plant sample, comprising:
   a support backing; and
   a first and second extraction pad releasably connected to the support backing, which first and second extraction pad are: (a) configured separately on the support backing in a non-overlying fashion relative to one another, such that the undersurface of each extraction pad is fully in contact with the support backing and (b) made of an abrasive material capable of effectively disrupting the physical integrity of a plant sample rubbed therebetween; and which first extraction pad is made of a material capable of collecting sap from the plant sample so disrupted and then capable of releasing said sample of sap for testing.

2. Apparatus according to claim 1, wherein each of the first and second extraction pads is a flat sheet of abrasive paper.

3. Apparatus according to claim 2, wherein the first extraction pad is peelably secured to the support backing.

4. Apparatus according to claim 3, wherein the first extraction pad includes a longitudinal fold line to facilitate folding the first extraction pad to reduce the size thereof.

5. Apparatus according to claim 4, wherein the first and second extraction pad are connected to separate support backings, which support backings are joined by a tear line to facilitate the tearing of one support backing from the other.

* * * * *

UNITED STATES PATENT AND TRADEMARK OFFICE
CERTIFICATE OF CORRECTION

PATENT NO.  : 5,047,207

DATED       : September 10, 1991

INVENTOR(S) : Lankow, et al.

It is certified that error appears in the above-identified patent and that said Letters Patent is hereby corrected as shown below:

On the title page, Item [75]:

Inventorship:   Change "Richard K. Lankow, Sally A. Miller, G. David Grothaus, Frank P. Petersen, Dennis R. Stocker, Stephanie L. Papa, James Donovan, Douglas Malik" as joint inventors to --Sally A. Miller--.

Signed and Sealed this

Twenty-ninth Day of June, 1993

Attest:

Attesting Officer

MICHAEL K. KIRK

Acting Commissioner of Patents and Trademarks